US006087292A

United States Patent [19]
Winter et al.

[11] Patent Number: 6,087,292
[45] Date of Patent: *Jul. 11, 2000

[54] METALLOCENE CATALYSTS COMPRISING INDENYL LIGANDS SUBSTITUTED WITH ELECTRONEGATIVE GROUPS

[75] Inventors: Andreas Winter, Glashuetten; Juergen Rohrmann, Kelkheim; Martin Antberg, Hofheim; Walter Spaleck, Liederbach; Wolfgang Anton Herrmann, Freising; Herbert Riepl, Dachau, all of Germany

[73] Assignee: Tangor GmbH, Germany

[*] Notice: This patent is subject to a terminal disclaimer.

[21] Appl. No.: 09/046,741

[22] Filed: Mar. 24, 1998

Related U.S. Application Data

[62] Division of application No. 08/475,752, Jun. 7, 1995, Pat. No. 5,763,542, which is a continuation of application No. 08/101,627, Aug. 3, 1993, Pat. No. 5,504,232.

[30] Foreign Application Priority Data

Aug. 3, 1992 [DE] Germany .............................. 42 25 648

[51] Int. Cl.$^7$ .................................................. B01J 31/00
[52] U.S. Cl. .......................... 502/117; 502/103; 502/152; 502/154; 502/155; 526/127; 526/160; 526/161; 526/943; 526/172
[58] Field of Search .................................... 526/127, 160; 502/117, 103, 152, 154, 155

[56] References Cited

U.S. PATENT DOCUMENTS

| | | | |
|---|---|---|---|
| 5,145,819 | 9/1992 | Winter et al. | 502/117 |
| 5,204,419 | 4/1993 | Tsutsui et al. | 526/153 |
| 5,278,264 | 1/1994 | Spaleck et al. | 526/127 |
| 5,304,614 | 4/1994 | Winter et al. | 526/127 |
| 5,328,969 | 7/1994 | Winter et al. | 526/127 |
| 5,329,033 | 7/1994 | Spaleck et al. | 556/53 |
| 5,576,260 | 11/1996 | Winter et al. | 502/117 |
| 5,786,432 | 7/1998 | Kuber et al. | 526/127 |

FOREIGN PATENT DOCUMENTS

| | | |
|---|---|---|
| 2017190 | 11/1990 | Canada . |
| 399348 | 11/1990 | European Pat. Off. . |

OTHER PUBLICATIONS

Lee et al., Electronic effects in Zeigler–Natta polymerization of propylene and ethylene using soluble metallocene catalysts, *Organometalics* vol. 11, No. 6, pp. 2115–2122, Jun. 1992.

Chemical Abstracts, vol. 117, 1992, Abstract No. 27208.

Lee et al, "Organometallics", vol. 11, No. 6, pp. 2155–2122 (1992).

J. March, "Advanced Organic Chemistry" Fourth Edition, Wiley, New York (1992) p. 14–16.

*Primary Examiner*—David W. Wu
*Assistant Examiner*—Roberto Rabago
*Attorney, Agent, or Firm*—Connolly Bove Lodge & Hutz LLP

[57] ABSTRACT

A highly effective catalyst system for the polymerization of olefins comprises a cocatalyst, preferably an aluminoxane, and a metallocene of the formula I

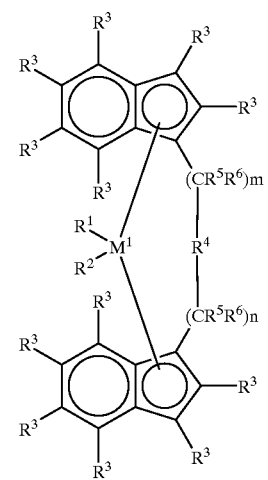

(I)

where $M^1$=Zr or Hf, $R^1$ and $R^2$=($C_1$–$C_3$)-alkyl or chlorine, $R^3$, with the proviso that at least one of the radicals $R^3$ is not hydrogen, is hydrogen, F, Cl, —$OR^7$, —$NR^7R^8$, —P(O)$R^7R^8$, —P($OR^7$)$_2$ or $SR^7$, $R^4$ is a

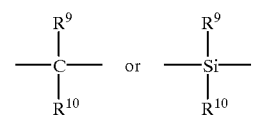

radical, and m plus n are zero or 1.

16 Claims, No Drawings

METALLOCENE CATALYSTS COMPRISING INDENYL LIGANDS SUBSTITUTED WITH ELECTRONEGATIVE GROUPS

This is a division of Ser. No. 08/475,752 filed Jun. 7, 1995, now U.S. Pat. No. 5,763,542, which is a continuation of Ser. No. 08/101,627, filed Aug. 3, 1993, now U.S. Pat. No. 5,504,232.

DESCRIPTION

The invention relates to a process for the preparation of olefin polymers and copolymers using metallocenes containing specifically substituted indenyl ligands.

The use of chiral metallocenes as a catalyst component in the polymerization of olefins is known and gives highly isotactic polyolefins of high crystallinity and high melting point (cf. Angew. Chem. 97 (1985) 507, German Patent 40 35 886.0).

If achiral metallocenes are used, atactic polymers are obtained which, due to their unbalanced and inadequate product properties, are only of restricted industrial importance.

Of considerable interest are products whose property profile is between these two extremes.

The object was to find a suitable process or a suitable catalyst system which enables the preparation of polymers of reduced crystallinity, increased impact strength, increased transparency, good flow properties at the processing temperature and reduced melting point.

The main applications of such polymers are plasticizer and lubricant formulations, hot-melt adhesive applications, coatings, seals, insulations, slush-molding compositions or sound-insulation materials.

The invention thus relates to a process for the preparation of an olefin polymer by polymerization or copolymerization of an olefin of the formula $R^a$—CH=CH—$R^b$, in which $R^a$ and $R^b$ are identical or different and are a hydrogen atom or a hydrocarbon radical having 1 to 14 carbon atoms, or $R^a$ and $R^b$, together with the atoms connecting them, can form a ring, at a temperature of from −60 to 200° C., at a pressure of from 0.5 to 100 bar, in solution, in suspension or in the gas phase, in the presence of a catalyst formed from a metallocene as transition-metal compound and a cocatalyst, wherein the metallocene is a compound of the formula I

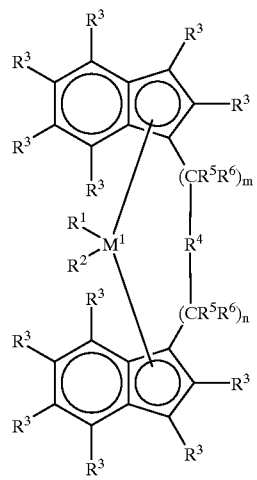

in which $M^1$ is a metal from group IVb, Vb or VIb of the Periodic Table, $R^1$ and $R^2$ are identical or different and are a hydrogen atom, a $C_1$–$C_{10}$-alkyl group, a $C_1$–$C_{10}$-alkoxy group, a $C_6$–$C_{10}$-aryl group, a $C_6$–$C_{10}$-aryloxy group, a $C_2$–$C_{10}$-alkenyl group, a $C_7$–$C_{10}$-arylalkyl group, a $C_7$–$C_{10}$-alkylaryl group, a $C_8$–$C_{40}$-arylalkenyl group or a halogen atom, $R^3$, in spite of the same indexing, are identical or different and are hydrogen or a polar or polarizable element which is more electronegative than hydrogen (electronegativity according to Allred and Rochow, from "Periodensystem der Elemente" [Periodic Table of the Elements], VCH-Verlagsgesellschaft, Weinheim, Germany (1985)), or are hydrocarbon radicals which contain a heteroatom which is more electronegative than hydrogen (electronegativity according to Allred and Rochow, from "Periodensystem der Elemente" [Periodic Table of the Elements], VCR-Verlagsgesellschaft, Weinheim, Germany (1985)), with the proviso that at least one of the radicals $R^3$ is not hydrogen, $R^4$ is

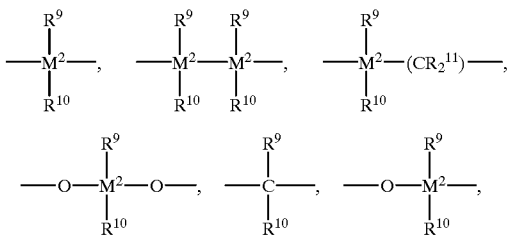

=$BR^9$, =$AlR^9$, —Ge—, —Sn—, —O—, —S—, =SO, =$SO_2$, =$NR^9$, =CO, =$PR^9$ or =$P(O)R^9$, where $R^9$, $R^{10}$ and $R^{11}$ are identical or different and are a hydrogen atom, a halogen atom, a $C_1$–$C_{10}$-alkyl group, a $C_1$–$C_{10}$-fluoroalkyl group, a $C_6$–$C_{10}$-aryl group, a $C_6$–$C_{10}$-fluoroaryl group, a $C_1$–$C_{10}$-alkoxy group, a $C_2$–$C_{10}$-alkenyl group, a $C_7$–$C_{40}$-arylalkyl group, a $C_8$–$C_{40}$-arylalkenyl group or a $C_7$–$C_{40}$-alkylaryl group, or $R^9$ and $R^{10}$ or $R^9$ and $R^{11}$, in each case together with the atoms connecting them, form a ring, $M^2$ is silicon, germanium or tin, $R^5$ and $R^6$ are identical or different and are as defined for $R^9$, and m and n are identical or different and are zero, 1 or 2, where m plus n is zero, 1 or 2.

Alkyl is straight-chain or branched alkyl. Halogen (halogenated) denotes fluorine, chlorine, bromine or iodine, preferably fluorine or chlorine.

The catalyst to be used for the process according to the invention comprises a cocatalyst and a metallocene of the formula I.

In the formula I, $M^1$ is a metal from group IVb, Vb or VIb of the Periodic Table, for example titanium, zirconium, hafnium, vanadium, niobium, tantalum, chromium, molybdenum or tungsten, preferably zirconium, hafnium or titanium.

$R^1$ and $R^2$ are identical or different and are a hydrogen atom, a $C_1$–$C_{10}$-, preferably $C_1$–$C_3$-alkyl group, a $C_1$–$C_{10}$-, preferably $C_1$–$C_3$-alkoxy group, a $C_6$–$C_{10}$-, preferably $C_6$–$C_8$-aryl group, a $C_6$–$C_{10}$-, preferably $C_6$–$C_8$-aryloxy group, a $C_2$–$C_{10}$-, preferably $C_2$–$C_4$-alkenyl group, a $C_7$–$C_{40}$-, preferably $C_7$–$C_{10}$-arylalkyl group, a $C_7$–$C_{40}$-, preferably $C_7$–$C_{12}$-alkylaryl group, a $C_8$–$C_{40}$-, preferably $C_8$–$C_{12}$-arylalkenyl group or a halogen atom, preferably chlorine.

The radicals $R^3$, in spite of the same indexing, are identical or different and are hydrogen or a polar or polarizable element which is more electronegative than hydrogen or is a hydrocarbon radical which contains a heteroatom which is more electronegative than hydrogen.

With the proviso that at least one of the radicals $R^3$ is not hydrogen, $R^3$ can be hydrogen, F, Cl, Br, preferably hydrogen, F or Cl, —$OR^7$, —$NR^7R^8$, —$P(O)R^7R^8$, —$P(OR^7)_2$ or $SR^7$, where $R^7$ and $R^8$ are hydrogen, a $C_1$–$C_{10}$-alkyl group, preferably a $C_1$–$C_6$-alkyl group, in particular a methyl group, a $C_1$–$C_{10}$-fluoroalkyl group, preferably a $CF_3$ group, a $C_6$–$C_{10}$-, preferably $C_6$–$C_8$-aryl group, a $C_6$–$C_{10}$-, preferably $C_6$–$C_8$-fluoroaryl group, in particular a pentafluorophenyl group, a $C_2$–$C_{10}$-, preferably $C_2$–$C_4$-alkenyl group, a $C_7$–$C_{40}$-, preferably $C_7$–$C_{10}$-arylalkyl group, a $C_8$–$C_{40}$-, preferably $C_8$–$C_{12}$-arylalkenyl group, or a $C_7$–$C_{40}$-, preferably $C_7$–$C_{12}$-alkylaryl group.

$R^4$ is

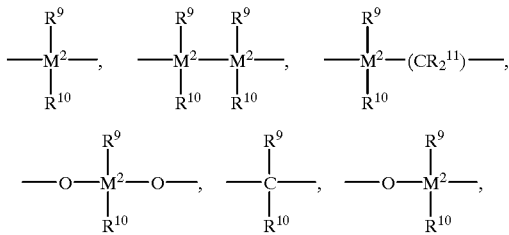

=$BR^9$, =$AlR^9$, —Ge—, —Sn—, —O—, —S—, =SO, =$SO_2$, =$NR^9$, =CO, =$PR^9$ or =$P(O)R^9$, where $R^9$, $R^{10}$ and $R^{11}$ are identical or different and are a hydrogen atom, a halogen atom, a $C_1$–$C_{10}$-, preferably $C_1$–$C_4$-alkyl group, in particular a methyl group, a $C_1$–$C_{10}$-fluoroalkyl group, preferably a $CF_3$ group, a $C_6$–$C_{10}$-, preferably $C_6$–$C_8$-aryl group, a $C_6$–$C_{10}$-fluoroaryl group, preferably a pentafluorophenyl group, a $C_1$–$C_{10}$-, preferably $C_1$–$C_4$-alkoxy group, in particular a methoxy group, a $C_2$–$C_{10}$-, preferably $C_2$–$C_4$-alkenyl group, a $C_7$–$C_{40}$-, preferably $C_7$–$C_{10}$-arylalkyl group, a $C_8$–$C_{40}$-, preferably $C_8$–$C_{12}$-arylalkenyl group or a $C_7$–$C_{40}$-, preferably $C_7$–$C_{12}$-alkylaryl group, or $R^9$ and $R^{10}$ or $R^9$ and $R^{11}$, in each case together with the atoms connecting them, form a ring.

$M^2$ is silicon, germanium or tin, preferably silicon or germanium.

$R^4$ is preferably =$CR^9R^{10}$, =$SiR^9R^{10}$, =$GeR^9R^{10}$, —O—, —S—, =SO,
=$PR^9$ or =$P(O)R^9$ and particularly preferably =$SiR^9R^{10}$ or =$CR^9R^{10}$.

$R^5$ and $R^6$ are identical or different and are as defined for $R^9$.

m and n are identical or different and are zero, 1 or 2, preferably zero or 1, where m plus n is zero, 1 or 2, preferably zero or 1.

Particularly preferred metallocenes are the compounds of the formulae A and B

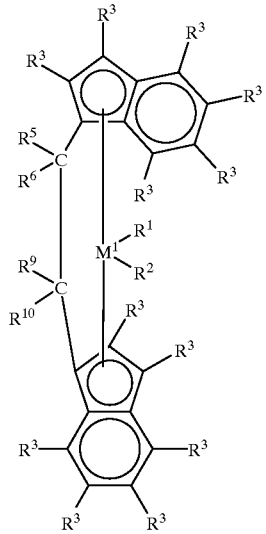

(A)

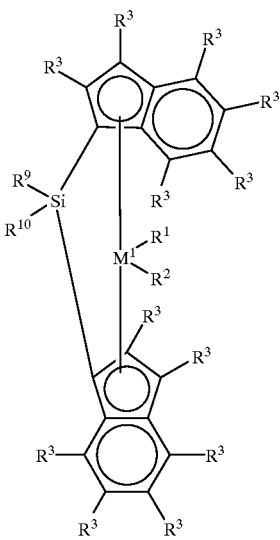

(B)

where $M^1$=Zr or Hf; $R^1$ and $R^2$=($C_1$–$C_3$)-alkyl or chlorine; $R^3$, with the proviso that at least one of the radicals $R^3$ is not hydrogen, =hydrogen, F, Cl, —$OR^7$, —$NR^7R^8$, —P(O)R$^7$R$^8$, —P(OR$^7$)$_2$ or SR$^7$, preferably hydrogen, F, Cl or OR$^7$; R$^5$, R$^6$, R$^7$, R$^8$, R$^9$ and R$^{10}$=(C$_1$–C$_{10}$)-alkyl or (C$_6$–C$_{10}$)-aryl, in particular hydrogen or methyl.

The chiral metallocenes are preferably employed as a racemate. However, it is also possible to use the pure R- or S-form. By means of these pure stereoisomeric forms, optically active polymer can be prepared. However, the meso-form of the metallocenes should be separated off, since the polymerization-active center (the metal atom) in these compounds is no longer chiral due to mirror symmetry at the central metal and is therefore incapable of producing a highly isotactic polymer. If the meso-form is not separated off, atactic polymer is formed in addition to isotactic polymers. For certain applications—for example soft moldings—this may be entirely desirable.

Resolution of the stereoisomers is known in principle.

The above-described metallocenes can be prepared in accordance with the following reaction scheme:

$$H_2R^c + \text{butylLi} \longrightarrow HR^cLi$$

$$\xrightarrow{X-(CR^5R^6)_{\overline{m}}-R^4-CR^5R^6-X}$$

$$H_2R^d + \text{butylLi} \longrightarrow HR^dLi$$

$$HR^c-(CR^5R^6)_{\overline{m}}-R^4-(CR^5R^6)_{\overline{n}}-R^dH \xrightarrow{2\text{ butyl Li}}$$

$$LiR^c-(CR^5R^6)_{\overline{m}}-R^4-(CR^5R^6)_{\overline{n}}-R^dLi \xrightarrow{M^1Cl_4}$$

[structure: (R$^5$R$^6$C)$_{\overline{m}}$–R$^c$, R$^4$, M, Cl, Cl, (R$^5$R$^6$C)$_{\overline{n}}$–R$^d$] $\xrightarrow{R^1Li}$

[structure with R$^1$, Cl] $\xrightarrow{R^2Li}$ [structure with R$^1$, R$^2$]

X=Cl, Br, I or O-tosyl;

H$_2$R$^c$, H$_2$R$^d$ = [indene structure with R$^3$ substituents]

The principal preparation processes are known from the literature; cf. Journal of Organometallic Chem. 288 (1985) 63–67, EP-A 320 762 and the working examples.

Starting compounds H$_2$R$^c$ and H$_2$R$^d$ are prepared, for example, as described in the working examples.

The cocatalyst used according to the invention is preferably an aluminoxane of the formula (II)

(II)

[structure: R$^{12}$–Al(R$^{12}$)–O–[Al(R$^{12}$)–O]$_p$–Al(R$^{12}$)–R$^{12}$]

for the linear type and/or of the formula (III)

(III)

[cyclic structure: –[O–Al(R$^{12}$)]$_{p+2}$–]

for the cyclic type, where, in the formulae (II) and (III), the radicals R$^{12}$ may be identical or different and are a C$_1$–C$_6$-alkyl group, a C$_6$–C$_{18}$-aryl group, benzyl or hydrogen, and p is an integer from 2 to 50, preferably from 10 to 35.

The radicals R$^{12}$ are preferably identical and are methyl, isobutyl, phenyl or benzyl, particularly preferably methyl.

If the radicals R$^{12}$ are different, they are preferably methyl and hydrogen or alternatively methyl and isobutyl, where hydrogen and isobutyl are preferably present to the extent of 0.01–40% (number of radicals R$^{14}$).

The aluminoxane can be prepared in various ways by known processes. One of the methods is, for example, to react an aluminum hydrocarbon compound and/or a hydridoaluminum hydrocarbon compound with water (in gas, solid, liquid or bound form—for example as water of crystallization) in an inert solvent (such as, for example, toluene). In order to prepare an aluminoxane containing different alkyl groups R$^{12}$, two different trialkylaluminum compounds (AlR$_3$+AlR'$_3$), in accordance with the desired composition, are reacted with water (cf. S. Pasynkiewicz, Polyhedron 9 (1990) 429 and EP-A 302 424).

The precise structure of the aluminoxanes II and III is unknown.

Irrespective of the preparation method, all aluminoxane solutions have in common a varying content of unreacted aluminum starting compound, which is in free form or as an adduct.

It is possible to preactivate the metallocene by means of an aluminoxane of the formula (II) and/or (III) before use in the polymerization reaction. This significantly increases the polymerization activity and improves the grain morphology.

The preactivation of the transition-metal compound is carried out in solution. The metallocene is preferably dissolved in a solution of the aluminoxane in an inert hydrocarbon. Suitable inert hydrocarbons are aliphatic or aromatic hydrocarbons. Preference is given to toluene and heptane.

The concentration of the aluminoxane in the solution is in the region of about 1% by weight to the saturation limit, preferably from 5 to 30% by weight, in each case based on the total solution. The metallocene can be employed in the same concentration, but is preferably employed in an amount of from 10$^{-4}$ to 1 mol per mole of aluminoxane. The preactivation time is from 5 minutes to 60 hours, preferably from 5 to 60 minutes. The reaction temperature is from −78° C. to 100° C., preferably from 0 to 70° C.

The metallocene can also be prepolymerized or applied to a support. For the prepolymerization, the (or one of the) olefin(s) employed in the polymerization is preferably used.

Examples of suitable supports are silica gels, aluminum oxides, solid aluminoxane or other inorganic support materials. Another suitable support material is a polyolefin powder in finely divided form.

Compounds of the formulae R$_x$NH$_{4-x}$BR'$_4$, R$_x$PH$_{4-x}$BR'$_4$, R$_3$CBR'$_4$ or BR'$_3$ can be used according to the invention as suitable cocatalysts instead of or in addition to an aluminoxane. In these formulae, x is a number from 1 to 4, preferably 3, and the radicals R are identical or different, preferably identical, and are C$_1$–C$_{10}$-alkyl or C$_6$–C$_{18}$-aryl, or 2 radicals R, together with the atom connecting them, form a ring, and the radicals R' are identical or different, preferably identical, and are $C_6$–$C_{18}$-aryl, which may be substituted by alkyl, haloalkyl or fluorine.

In particular, R is ethyl, propyl, butyl or phenyl and R' is phenyl, pentafluorophenyl, 3,5-bistrifluoromethylphenyl, mesityl, xylyl or tolyl (cf. EP-A 277 003, EP-A 277 004 and EP-A 426 638).

When the abovementioned cocatalysts are used, the actual (active) polymerization catalyst comprises the product of the reaction of the metallocene and one of said compounds. This reaction product is therefore prepared first, preferably outside the polymerization reactor, in a separate step using a suitable solvent.

In principle, suitable cocatalysts are according to the invention any compounds which, due to their Lewis acidity, are able to convert the neutral metallocene into a cation and stabilize the latter ("labile coordination"). In addition, the cocatalyst or the anion formed therefrom must not undergo any further reactions with the metallocene cation formed (cf. EP-A 427 697).

In order to remove catalyst poisons present in the olefin, purification by means of an alkylaluminum compound, for example $AlMe_3$, $Al(i-Bu)_3$ or $AlEt_3$, is advantageous. This purification can be carried out either in the polymerization system itself, or the olefin is brought into contact with the Al compound before addition to the polymerization system and subsequently removed again.

The polymerization or copolymerization is carried out in a known manner in solution, in suspension or in the gas phase, continuously or batchwise, in one or more steps, at a temperature of from −60 to 200° C., preferably from 30 to 80° C. Olefins of the formula $R^a$—CH=CH—$R^b$ are polymerized or copolymerized. In this formula, $R^a$ and $R^b$ are identical or different and are a hydrogen atom or an alkyl radical having 1 to 14 carbon atoms. However, $R^a$ and $R^b$, together with the carbon atoms connecting them, can form a ring. Examples of such olefins are ethylene, propylene, 1-butene, 1-hexene, 4-methyl-1-pentene, 1-octene, norbornene and norbornadiene. In particular, propylene and ethylene are polymerized.

If necessary, hydrogen is added as molecular weight regulator and/or to increase the activity. The total pressure in the polymerization system is from 0.5 to 100 bar. Polymerization is preferably carried out in the industrially particularly relevant pressure range of from 5 to 64 bar.

The metallocene is used in a concentration, based on the transition metal, of from $10^{-3}$ to $10^{-8}$ mol, preferably from $10^{-4}$ to $10^{-7}$ molt of transition metal per $dm^3$ of solvent or per $dm^3$ of reactor volume. The aluminoxane is used in a concentration of from $10^{-5}$ to $10^{-1}$ mol, preferably from $10^{-4}$ to $10^{-2}$ mol, per $dm^3$ of solvent or per $dm^3$ of reactor volume. The other cocatalysts mentioned are used in approximately equimolar amounts with respect to the metallocene. In principle, however, higher concentrations are also possible.

If the polymerization is carried out as a suspension or solution polymerization, an inert solvent which is customary for the Ziegler low-pressure process is used. For example, the polymerization is carried out in an aliphatic or cycloaliphatic hydrocarbon; examples of these which may be mentioned are propane, butane, pentane, hexane, heptane, isooctane, cyclohexane and methylcyclohexane.

If is furthermore possible to use a benzine or hydrogenated diesel oil fraction. Toluene can also be used. The polymerization is preferably carried out in the liquid monomer.

If inert solvents are used, the monomers are metered in as gases or liquids.

The polymerization can have any desired duration, since the catalyst system to be used according to the invention exhibits only a slight time-dependent drop in polymerization activity.

The process according to the invention is distinguished by the fact that the metallocenes described give polymers having the desired property profile, preferably in the industrially relevant temperature range between 30 and 80° C. with high polymerization activity.

These polymers preferably have isotactic block lengths of <50.

The examples below are intended to illustrate the invention in greater detail.

The following abbreviations are used:

VI=viscosity index in $cm^3/g$ $M_w$=weight average molecular weight in g/mol determined by gel permeation chromatography $M_w/M_n$=molecular weight dispersity m.p.=melting point, determined by DSC (heating/cooling rate 20° C./min)

II=isotactic index (II=mm+1/2 mr), determined by $^{13}$C-NMR spectroscopy $n_{iso}$=isotactic block length (1/+2 mm/mr)

Synthesis of the metallocenes used in the examples:

EXAMPLE A

Dimethylbis(5(6)-fluoroindenyl)silane (1)

10.7 ml (26.8 mmol) of a 2.5 M butyllithium solution in hexane were added at room temperature to a solution of 3.6 g (26.8 mmol) of 6-fluoroindene (prepared by the method of Marechal et al., Bull. Soc. Chim. Fr. 11 (1973) 3092) in 35 ml of diethyl ether, and the mixture was stirred at this temperature for 1 hour. The solution was added dropwise to a solution of 1.7 g (13.4 mmol) of dimethyldichlorosilane in 10 ml of diethyl ether, and the mixture was stirred at room temperature for 17 hours, poured into ice water and extracted with ether. The oil which remained after the solvent had been stripped off was chromatographed on 150 g of silica gel 60. Using hexane/5% ethyl acetate as eluent, 3.1 g (71%) of the ligand system 1 were isolated as a brownish oil. The $^1$H-NMR spectrum shows a strong isomer mixture (constitutional isomers due to fluorine in the 5,5'-, 5,6'- or 6,6'-position, diastereomers due to a center of chirality in the 1-position and double-bond isomers). $^{19}$F-NMR spectrum ($CDCl_3/CFCl_3$, 94.2 MHz): −118.7 (m), −119.3 (m).

rac-Dimethylsilanediylbis(5(6)-fluoroindenyl)zirconium dichloride (2)

7.6 ml (18.5 mmol) of a 2.5 M butyllithium solution in hexane were added at 0° C. to a solution of 3.0 g (9.3 mmol) of the ligand system 1 in 50 ml of diethyl ether, and the mixture was stirred at room temperature overnight. After the solvent had been stripped off, the dark-red residue was dried for a long time in an oil-pump vacuum and washed with hexane. The pale-brown, extremely air-sensitive powder was added at −78° C. to a suspension of 2.2 g (9.3 mmol) of $ZrCl_4$ in 40 ml of methylene chloride, and the mixture was warmed to room temperature over the course of 4 hours. After the mixture had been stirred at this temperature for 1 hour, it was filtered through a G3 frit, the solid was washed with 50 ml of methylene chloride, and the orange filtrate was evaporated to dryness, giving 2.9 g (64%) of the metallocene 2 as a rac/meso mixture in the ratio 1:1. The orange powder was stirred at room temperature with 6 ml of tetrahydrofuran and filtered through a G4 frit. The orange precipitate was washed twice with 1 ml of THF in each case and dried in an oil-pump vacuum, giving 700 mg (15%) of the pure racemate 2. $^1$H-NMR spectrum (CDCl$_3$): (Constitutional isomers due to fluorine in the 5,5'-, 5,6'- or 6,6'-position) 6.9–7.8 (m, aromatic H, β-IndH), 6.1 (m, α-IndH), 1.12 (m, SiCH$_3$). Mass spectrum (EI, 70 eV): 484 M$^+$, correct decomposition, correct isotope pattern.

EXAMPLE B

Dimethylbis(4(7)-fluoroindenyl)silane (3)

18.8 ml (47 mmol) of a 2.5 M butyllithium solution in hexane were added at room temperature to a solution of 6.3 g (47 mmol) of 7-fluoroindene (prepared from 2-fluorocinnamic acid analogously to the method of Dewar et al., J. Amer. Chem. Soc., 95 (1973) 7353) in 50 ml of diethyl ether, and the mixture was stirred at room temperature for 1 hour and added dropwise to a solution of 3.0 g (23.5 mmol) of dimethyldichlorosilane in 15 ml of diethyl ether. After the mixture had been stirred for 17 hours, it was worked up and purified analogously to Example A, giving 4.7 g (72%) of the ligand system 3 as a brownish oil. The $^1$H-NMR spectrum shows a strong isomer mixture (constitutional isomers due to fluorine in the 4,4'-, 4,7'- or 7,7'-position, diastereomers due to a center of chirality in the 1-position and double-bond isomers). $^{19}$F-NMR spectrum (CDCl$_3$/CFCl$_3$, 94.2 MHz): –116 (m), –122 (m).

rac-Dimethylsilanediylbis(4(7)-fluoroindenyl)zirconium dichloride (4)

1.0 g (3.1 mmol) of the ligand system 3 were reacted analogously to (2) with 2.7 ml of butyllithium (2.5 M) and 0.70 g (3.0 mmol) of zirconium tetrachloride. The crude product obtained was 1.3 g (89%) of the metallocene 4 as a rac/meso mixture in the ratio 1:1 (yellow-orange powder). Recrystallization from toluene gave the pure racemate. $^1$H-NMR spectrum (CDCl$_3$): (Constitutional isomers due to fluorine in the 4,4'-, 4,7'- or 7,7'-position) 6.7–7.4 (m, aromatic H), 6.1 (m, α-IndH), 1.12 (m, SiCH$_3$). Mass spectrum (EI, 70 eV): 484 M$^+$, correct decomposition, correct isotope pattern.

EXAMPLE C

Dimethylbis(5,6-dimethoxyindenyl)silane (5)

23.6 ml (59 mmol) of a 2.5 M butyllithium solution in hexane were added at room temperature to a solution of 10.4 g (59 mmol) of 5,6-dimethoxyindene (prepared by the method of Eberson et al., Acta Chem. Scand. B 30 (1976) 527) in 150 ml of THF, and the mixture was stirred at room temperature for 2 hours and added dropwise to a solution of 3.6 ml (29.5 mmol) of dimethyldichlorosilane in 20 ml of THF. The mixture was stirred overnight, poured into ice water and extracted with ether. The extracts were dried using Na$_2$SO$_4$, and the solvent was stripped off. The residue was stirred with diethyl ether, 2.2 g (18%) of the ligand system crystallizing. $^1$H-NMR spectrum (CDCl$_3$, 400 MHz): (2 diastereomers in the ratio 1:1) 6.82–6.87 (β-IndH), 6.55 (dd, α-IndH), 6.34 (dd, α-IndH), 3.91 (s, OCH$_3$), 3.90 (s, OCH$_3$), 3.87 (s, OCH$_3$), 3.84 (s, OCH$_3$), 3.53 (m, CH), 3.51 (m, CH), –0.05 (s, SiCH$_3$), –0.24 (s, SiCH$_3$), –0.41 (s, SiCH$_3$). Mass spectrum: 408 M$^+$, correct decomposition, correct isotope pattern.

Chromatography of the mother liquor on 400 g of silica gel 60 gave a further 4.41 g of the ligand system 5 using methylene chloride/5% ethyl acetate as eluent. Separation into the isomers was likewise possible using this eluent mixture. The total yield was 6.61 g (55%).

rac-Dimethylsilanediylbis(5,6-dimethoxyindenyl)zirconium dichloride (6)

4.7 ml (11.8 mmol) of a 2.5 M butyllithium solution in hexane were added at room temperature to a solution of 2.2 g (5.38 mmol) of the ligand system 5 in 65 ml of diethyl ether and 20 ml of THF, and the mixture was stirred at room temperature for 5 hours. The dilithio salt which had precipitated was filtered off, washed with a little diethyl ether and dried in an oil-pump vacuum. The powder was added at –78° C. to a suspension of 1.0 g (4.3 mmol) of ZrCl$_4$ in 15 ml of methylene chloride. The mixture was warmed to room temperature over the course of 2 hours and stirred at this temperature for a further 3 hours and filtered through a G4 frit, and the solid was washed with 20 ml of methylene chloride. The filtrate was evaporated by half and left to crystallize at –35° C., giving 0.90 g (35%) of the metallocene 6 as a rac/meso mixture in the ratio 3:1 (yellow-orange crystals). Recrystallization from methylene chloride gives a pure racemate. $^1$H-NMR spectrum (100 MHz, CDCl$_3$): 6.57–6.85 (m, aromatic H), 6.75 (β-IndH), 5.82 (d, 2, α-IndH), 3.95 (s, OCH$_3$), 3.85 (s, OCH$_3$), 1.10 (s, SiCH$_3$).

EXAMPLE D 1,2-Bis(2-methoxyindenyl)ethane (7)

99 ml (158 mmol) of a 1.6 M butyllithium solution in hexane were added to a solution of 21.2 g (158 mmol) of 2-methoxyindene (prepared as described in J. Am. Chem. Soc. 106 (1984) 6702) in 200 ml of THF, and the mixture was stirred at room temperature for 2 hours. 6.84 ml (79 mmol) of 1,2-dibromoethane in 50 ml of THF were subsequently added dropwise at –78° C. The mixture was stirred at room temperature for 30 hours, all the solvent was removed, and the residue was extracted with toluene. Pentane was added to the filtrate, a byproduct (spiro compound) depositing as an oil. The supernatant solution was evaporated, and the starting material and byproduct were removed by distillation, leaving, as residue, 11.3 g (45%) of the ligand system 7.

1,2-Ethanediylbis(2-methoxyindenyl)zirconium dichloride (8)

3.18 g (10 mmol) of the ligand system 7 were dissolved in 100 ml of THF, 12.5 ml (20 mmol) of a 1.6 M butyllithium solution in hexane were added, and the mixture was stirred at 60° C. for 5 hours. In parallel, 3.77 g (10 mmol) of ZrCl$_4$.2THF were dissolved in 100 ml of THF. The two solutions were added dropwise and synchronously to 20 ml of THF over the course of 2.5 hours. The mixture was left to stand overnight and evaporated, and the residue was extracted with toluene. During evaporation, 1.6 g (35%) of the metallocene 8 crystallized as a rac/meso mixture 1:1. Recrystallization from toluene gives the pure racemate. $^1$H-NMR spectrum (100 MHz, CDCl$_3$): (rac/meso 1:1) 6.8–7.6 (m, aromatic H), 6.1 (s, β-IndH), 6.0 (s, β-IndH), 4.0 (s, OCH$_3$), 3.7 (s, OCH$_3$), 3.5–3.8 (ml C$_2$H$_4$).

EXAMPLE E 1,2-Bis(3-methoxyindenyl)ethane (9)

10.9 g (75 mmol) of 3-methoxyindene (prepared as described in J. Am. Chem. Soc. 106 (1984) 6702) were dissolved in 100 ml of THF, and 47 ml (75.2 mmol) of a 1.6 M butyllithium solution in hexane were added. The mixture was stirred at 50° C. for 2 hours, 3.25 ml (30.1 mmol) of 1,2-dibromoethane in 30 ml of THF were added dropwise at –78° C., and the mixture was warmed to room temperature. The solvent was stripped off, and the product was extracted with toluene. Yield 6.2 g (64%).

1,2-Ethanediylbis(3-methoxyindenyl)zirconium dichloride (10)

A solution of 3.85 g (12.1 mmol) of the ligand system 9 was reacted with 16 ml of butyllithium and 4.88 g of ZrCl$_4$ and worked up analogously to (8), giving 1.8 g (31%) of the rac/meso mixture 1:1. The pure racemate was obtainable by recrystallization from toluene. $^1$H-NMR spectrum (100 MHz, CDCl$_3$): (rac/meso 1:1) 6.9–7.5 (m, aromatic H), 5.9 (s, α-IndH), 5.7 (s, α-IndH), 3.9 (s, OCH$_3$), 3.8 (s, OCH$_3$), 3.5–4.0 (m, C$_2$H$_4$).

EXAMPLE F
Dimethylbis(5-chloroindenyl)silane (11)

23 ml of a 1.6 M butyllithium solution were added at 0° C. to a solution of 5.35 g (35.7 mmol) of 5-chloroindene (Bull. Soc. Chim. Fr. 11 (1973) 3096) in 40 ml of ether, and the mixture was stirred at room temperature for 4 hours. The orange solution was added dropwise at 0° C. to a solution of 2.35 g (18.3 mmol) of dimethyldichlorosilane in 40 ml of ether. The mixture was stirred overnight and worked up analogously to Example A. Chromatography on silica gel 40 using an eluent mixture of hexane/methylene chloride 10:1 to 10:3 gave, after unreacted starting material, 6.22 g (49%) of the ligand system 11 as a yellowish oil (isomers). $^1$H-NMR spectrum (100 MHz, CDCl$_3$): 7.42 (s), 7.41 (s), 7.32 (s), 7.21 (s), 7.19 (s), 7.15 (s), 7.14 (s), 6.83 (m), 6.63 (d), 3.21 (s, 2 H); 0.09 (s), −0.06 (s), −0.24 (s), −0.27 (s).

rac-Dimethylsilanediylbis(5-chloroindenyl)zirconium dichloride (12)

A solution of 10 ml of a 1.6 M butyllithium solution in 30 ml of THF was added at 0° C. to a solution of 700 mg (1.96 mmol) of the ligand system 11 in 10 ml of ether. The mixture was stirred at room temperature for 3 hours, the solvent was stripped off to a slightly viscous consistency with vigorous stirring, and 60 ml of hexane were added. The precipitate was filtered off at 0° C. and dried for one day in high vacuum, giving 483 mg (60%) of the dilithio salt as a brown powder. The latter was reacted with 304 mg of ZrCl$_4$ analogously to (2). Recrystallization from toluene gave 120 mg (17%) of the racemate 12 in the form of a yellow microcrystalline powder. $^1$H-NMR spectrum (100 MHz, CDCl$_3$): 7.41 (s), 7.34 (s), 7.19 (s), 7.18 (s), 7.08 (s), 7.04 (s), 6.92 (m), 6.09 (d, $^1J_{HH}$=3.34 Hz), 1.1 (s). $^{13}$C-NMR spectrum: 146.6, 136.8, 128.0, 127.2, 126.8, 125.1, 124.9, 121.5, 120.7, −4.7.

POLYMERIZATION EXAMPLES

Example 1

A dry 16 dm$^3$ reactor was flushed with propylene and charged with 10 dm$^3$ of liquid propylene. 30 cm$^3$ of a toluene solution of methylaluminoxane (corresponding to 40 mmol of Al, mean degree of oligomerization was p=19) were then added, and the batch was stirred at 30° C. for 15 minutes.

In parallel, 24.1 mg of rac-dimethylsilanediylbis-(5(6)-fluoroindenyl) zirconium dichloride (Example A, (2)) were dissolved in 15 cm$^3$ of a toluene solution of methylaluminoxane (20 mmol of Al) and left to stand for 15 minutes for preactivation.

The solution was then introduced into the reactor, the reactor contents were heated to 70° C. (10° C./min) by supply of heat, and the polymerization system was kept at 70° C. for 1.5 hours. The reaction was terminated by rapidly removing the excess monomer as a gas.

The activity of the metallocene was 67.8 kg of PP/g of metallocene×h. VI=40 cm$^3$/g; M$_w$=25,800 g/mol; M$_w$/M$_n$=2.3; m.p.=134° C.; II=88.5%; n$_{iso}$=16.

Example 2

Example 1 was repeated using 74.4 mg of the metallocene. The polymerization temperature was 30° C. and the polymerization duration was 4 hours. The activity of the metallocene was 4.0 kg of PP/g of metallocene×h. VI=82 cm$^3$/g; M$_w$=47,900 g/mol; M$_w$/M$_n$=2.8; m.p.=143° C.; II=94.7%; n$_{iso}$=34.

Example 3

A dry 1.5 dm$^3$ reactor was flushed with nitrogen and charged at 20° C. with 0.75 dm$^3$ of a benzine fraction having the boiling range 100–120° C. from which the aromatic components had been removed. The gas space of the reactor was then flushed free of nitrogen by injecting 2 bar of ethylene and decompressing the reactor, and repeating this operation 5 times. 3.75 cm$^3$ of a toluene solution of methylaluminoxane (5 mmol of Al, p=19) were then added. The reactor was heated to 30° C. (over the course of 15 minutes) with stirring, and a total pressure of 5 bar was established by adding ethylene at a stirring rate of 500 rpm.

In parallel, 0.125 mg of the metallocene rac-dimethylsilanediylbis(5(6)-fluoroindenyl)zirconium dichloride were dissolved in 1.25 cm$^3$ of a toluene solution of methylaluminoxane (1.67 mmol of Al, p=19) and left to stand for 15 minutes to achieve full reaction. The solution was then introduced into the reactor. The polymerization system was heated to 70° C. and kept at this temperature for 1 hour by appropriate cooling. The pressure was kept constant at 5 bar during this time by appropriate supply of ethylene. The reaction was then terminated by addition of 2 ml of isopropanol, and the polymer was filtered off and dried in vacuo. The activity of the metallocene was 248 kg of PE/g of metallocene×h. VI=221 cm$^3$/g; M$_w$=147,000 g/mol; /M$_w$/M$_n$=3.1.

Example 4

Example 1 was repeated, but the metallocene used was 50.1 mg of rac-1,2-ethanediylbis(2-methoxyindenyl)-zirconium dichloride (Example D, (8)). The polymerization duration was 3 hours.

The metallocene activity was 12.8 kg of PP/g of metallocene×h. VI=34 cm$^3$/g; M$_w$=24,500 g/mol; M$_w$/M$_n$=2.0; m.p.=127° C.; II=92.4%; n$_{iso}$=22.

Example 5

Example 4 was repeated using 107.6 mg of metallocene at a polymerization temperature of 50° C.

The metallocene activity was 1.1 kg of PP/g of metallocene×h. VI=52 cm$^3$/g; M$_w$=44,500 g/mol; M$_w$/M$_n$=2.1; m.p.=142° C.

Example 6

Example 4 was repeated using 221.8 mg of metallocene at a polymerization temperature of 30° C.

The metallocene activity was 0.5 kg of PP/g of metallocene×h. VI=85 cm$^3$/g; M$_w$=80,000 g/mol; M$_w$/M$_n$=2.7; m.p.=152° C.; II=96.3%, n$_{iso}$=46.

Example 7

Example 3 was repeated, but the metallocene used was the same amount of rac-1,2-ethanediylbis(2-methoxyindenyl)-zirconium dichloride.

The metallocene activity was 59 kg of PE/g of metallocene×h. VI=385 cm$^3$/g.

Example 8

Example 1 was repeated, but the metallocene used was 90.2 mg of rac-dimethylsilanediylbis(5,6-dimethoxyindenyl)zirconium dichloride (Example C, (6)).

The metallocene activity was 2.3 kg of PP/g of metallocene×h. VI=28 cm$^3$/g; $M_w$=21,700 g/mol; $M_w/M_n$=3.3; m.p.=139° C.; II=92.9%.

Example 9

Example 1 was repeated, but the metallocene used was 47.0 mg of rac-dimethylsilanediylbis(5-chloroindenyl)-zirconium dichloride (Example F).

The metallocene activity was 43 kg of PP/g of metallocene×h. VI=20 cm$^3$/g; $M_w$=9,900 g/mol; $M_w/M_n$=1.9; m.p.=141° C.; II=96.0%; $n_{iso}$=41.

Example 10

Example 3 was repeated, but the metallocene used was rac-dimethylsilanediylbis(5-chloroindenyl)zirconium dichloride (Example F).

The metallocene activity was 50 kg of PE/g of metallocene×h. $M_w$=148,000 g/mol; $M_w/M_n$=3.1.

Example 11

Example 1 was repeated, but the metallocene used was 22.9 mg of rac-dimethylsilanediylbis(4(7)-fluoroindenyl)-zirconium dichloride (Example B, (4)).

The metallocene activity was 57 kg of PP/g of metallocene×h. VI=46 cm$^3$/g; $M_w$=29,400 g/mol; $M_w/M_n$=2.2; m.p.=135° C.; II=89.7%; $n_{iso}$=19.

Example 12

Example 1 was repeated, but the metallocene employed was 57.9 mg of rac-dimethylsilanediylbis(5,6-dichloroindenyl)zirconium dichloride.

The metallocene activity was 27.5 kg of PP/g of metallocene×h. VI=42 cm$^3$/g; $M_w$=39,500 g/mol; $M_w/M_n$=2.0; m.p.=129° C.; II=85.3%; $n_{iso}$=12.

We claim:

1. A catalyst comprising a cocatalyst and a metallocene of the formula I

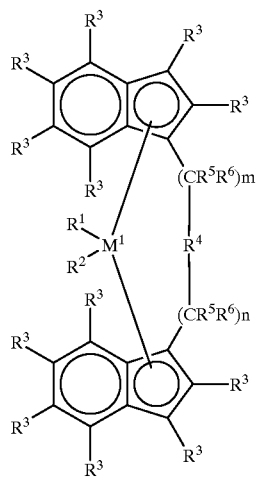

(I)

in which
$M^1$ is a metal from group IVb, Vb or VIb of the Periodic Table, $R^1$ and $R^2$ are identical or different and are a hydrogen atom, a $C_1$–$C_{10}$-alkyl group, a $C_1$–$C_{10}$-alkoxy group, a $C_6$–$C_{10}$-aryl group, a $C_8$–$C_{10}$-aryloxy group, a $C_2$–$C_{10}$-alkenyl group, a $C_7$–$C_{40}$-arylalkyl group, a $C_7$–$C_{40}$-alkylaryl group, a $C_8$–$C_{40}$-arylalkenyl group or a halogen atom, $R^3$ in spite of the same indexing, are identical or different and are hydrogen or a polar or polarizable element which is more electronegative than hydrogen, or are hydrocarbon radicals which contain a heteroatom which is more electronegative than hydrogen, with the proviso that $R^3$ is different from —$OR^7$, where $R^7$ is hydrogen, a $C_1$–$C_{10}$-alkyl group, a $C_1$–$C_{10}$-fluoroalkyl group, a $C_6$–$C_{10}$-aryl group, a $C_6$–$C_{10}$-fluoroaryl group, a $C_2$–$C_{10}$-alkenyl group, a $C_7$–$C_{40}$-arylalkyl group, a $C_8$–$C_{40}$-arylalkenyl group or a $C_7$–$C_{40}$-alkylaryl group and that at least one of the radicals $R^3$ on the six-membered ring of the indenyl ligand not hydrogen, $R^4$

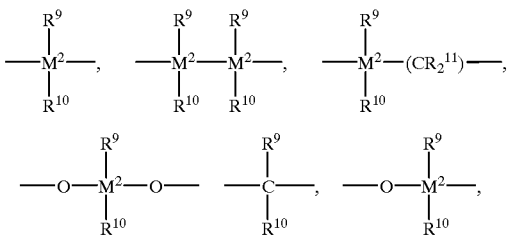

=$BR^9$, =$AlR^9$, —Ge—, —Sn—, —O—, —S—, =SO, =SO$_2$, =$NR^9$, =CO, =$PR^9$ or =$P(O)R^9$, where $R^9$, $R^{10}$ and $R^{11}$ are identical or different and are a hydrogen atom, a halogen atom,
a $C_1$–$C_{10}$-alkyl group, a $C_1$–$C_{10}$-fluoroalkyl group, a $C_6$–$C_{10}$-aryl group, a
$C_6$–$C_{10}$-fluoroaryl group, a $C_1$–$C_{10}$-alkoxy group, a $C_2$–$C_{10}$- alkenyl group,
a $C_7$–$C_{40}$-arylalkyl group, a $C_8$–$C_{40}$-arylalkenyl group or a $C_7$–$C_{40}$-alkylaryl group, or $R^9$ and $R^{10}$ or $R^9$ and $R^{11}$, in each case together with the atoms connecting them, form a ring, $M^2$ is silicon, germanium or tin, $R^5$ and $R^6$ are identical or different and are as defined for $R^9$, and m and n are identical or different and are zero, 1 or 2, where m plus n is zero, 1 or 2.

2. The catalyst as claimed in claim 1, wherein $R^1$ and $R^2$ are identical or different and are a $C_1$–$C_3$-alkyl group, a $C_1$–$C_3$-alkoxy group, a $C_6$–$C_8$-aryl group, a $C_6$–$C_8$-aryloxy group, a $C_2$–$C_4$-alkenyl group, a $C_7$–$C_{10}$-arylalkyl group, a $C_8$–$C_{12}$-arylalkenyl group or a chlorine atom.

3. The catalyst as claimed in claim 1, wherein
$M^1$ is Zr or Hf,
$R^1$ and $R^2$ are identical or different and are ($C_1$–$C_3$)-alkyl or chlorine.

4. The catalyst as claimed in claim 1, wherein
$R^3$ is hydrogen, F, Cl, Br, —$NR^7R^8$, —$P(O)R^7R^8$, —$P(OR^7)_2$ or $SR^7$ and wherein $R^8$ has the same definition as $R^7$.

5. The catalyst as claimed in claim 4, wherein $R^3$ is hydrogen, F or Cl.

6. The catalyst as claimed in claim 1, wherein $R^7$ is a methyl group.

7. The catalyst as claimed in claim 1, wherein $R^9$, $R^{10}$ and $R^{11}$ are identical or different and are a hydrogen atom, a $C_1$–$C_4$-alkyl group, a $CF_3$ group, a $C_6$–$C_8$-aryl group, a pentafluorophenyl group, a $C_1$–$C_4$-alkoxy group, a $C_2$–$C_4$-alkenyl group, a $C_7$–$C_{10}$-arylalkyl group, a $C_8$–$C_{12}$-arylalkenyl group or a $C_7$–$C_{12}$-alkylaryl group.

8. The catalyst as claimed in claim 1, wherein $M^2$ is silicon or germanium.

9. The catalyst as claimed in claim 8, wherein $R^4$ is $=CR^9R^{10}$, $=SiR^9R^{10}$, $=GeR^9R^{10}$, —O—, —S—, $=SO$, $=PR^9$ or $=P(O)R^9$.

10. The catalyst as claimed in claim 1, wherein the metallocene compound is of the formula (A) or (B)

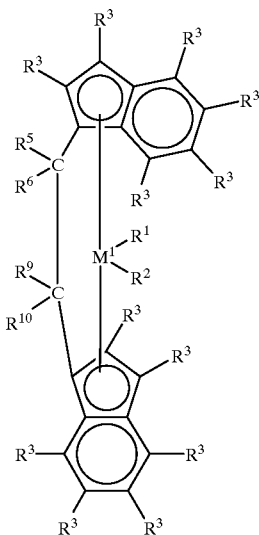

(A)

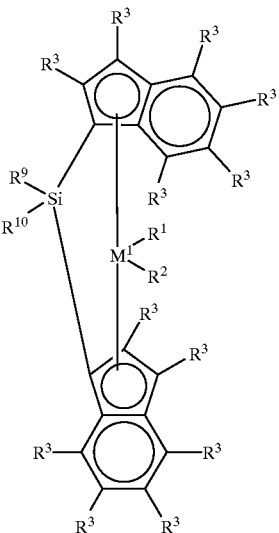

(B)

where
$M^1$ is Zr or Hf;
$R^1$ and $R^2$ are identical or different and are $(C_1$–$C_3)$-alkyl or chlorine;
$R^3$, with the proviso that at least one of the radicals $R^3$ on the six-membered ring of the indenyl lipid is not hydrogen, are hydrogen, F, Cl, $-NR^7R^8$, $-P(O)R^7R^8$, $-P(OR^7)_2$ or $SR^7$; and
$R^5$, $R^6$, $R^7$, $R^8$, $R^9$ and $R^{10}$ are identical or different and are $(C_1$–$C_{10})$-alkyl or $(C_6$–$C_{10})$-aryl.

11. The catalyst as claimed in claim 1, wherein the metallocene is rac-dimethylsilanediylbis(fluoroindenyl) zirconium dichloride wherein the fluorine is in the 5,5', 5,6' or 6,6' positions.

12. The catalyst as claimed in claim 1, wherein the metallocene is rac-dimethylsilanediylbis(fluoroindenyl) zirconium dichloride wherein the fluorine is in the 4,4', 4,7' or 7,7' positions.

13. The catalyst as claimed in claim 1, wherein the metallocene is rac-dimethylsilanediylbis(5-chloroindenyl) zirconium dichloride.

14. The catalyst as claimed in claim 1, wherein the at least one $R^3$ located at the 4, 5, 6 or 7 position of the indenyl ligand is not hydrogen.

15. The catalyst as claimed in claim 1, wherein the at least one $R^3$ located at the 5 or 6 position of the indenyl ligand is not hydrogen.

16. The catalyst as claimed in claim 1, wherein the at least one $R^3$ located at the 5 position of the indenyl ligand is not hydrogen.

* * * * *

UNITED STATES PATENT AND TRADEMARK OFFICE
CERTIFICATE OF CORRECTION

PATENT NO. : 6,087,292
DATED : July 11, 2000
INVENTOR(S) : Andreas Winter, Juergen Rohrmann, Martin Antberg, Walter Spaleck, Wolfgang Anton Herrmann, Herbert Riepl It is certified that error appears in the above-identified patent and that said Letters Patent is hereby corrected as shown below:

Title page, Assignee, Item [73],
"Tangor" should read -- Targor --.

Abstract,
Line 6, "is hydrogen" should read -- = hydrogen --.

Column 14,
Line 8, "alKenyl" should read -- alkenyl --.
Line 22, (last line of definition of $R^3$), the word "is" should be inserted before the word "not".
Line 23, the word "is" should be inserted after "$R^4$".

Column 16,
Line 30, the word "lipid" should be "ligand".

Signed and Sealed this

Fourteenth Day of August, 2001

*Attest:*

NICHOLAS P. GODICI
*Attesting Officer*     *Acting Director of the United States Patent and Trademark Office*